United States Patent
Felt et al.

(10) Patent No.: US 8,425,448 B2
(45) Date of Patent: Apr. 23, 2013

(54) ADJUSTING PH IN A METHOD OF SEPARATING WHOLE BLOOD

(75) Inventors: Thomas Felt, Boulder, CO (US); Peter Pihlstedt, Stockholm (SE); Bruce Gibbs, Arvada, CO (US)

(73) Assignee: Terumo BCT, Inc., Lakewood, CO (US)

( * ) Notice: Subject to any disclaimer, the term of this patent is extended or adjusted under 35 U.S.C. 154(b) by 540 days.

(21) Appl. No.: 11/668,715

(22) Filed: Jan. 30, 2007

(65) Prior Publication Data

US 2007/0179423 A1 Aug. 2, 2007

Related U.S. Application Data

(60) Provisional application No. 60/766,586, filed on Jan. 30, 2006.

(51) Int. Cl.
A61M 1/00 (2006.01)
A61M 37/00 (2006.01)
B04B 11/00 (2006.01)
B04B 11/02 (2006.01)
B04B 15/00 (2006.01)

(52) U.S. Cl.
USPC ....... 604/6.04; 604/6.01; 604/6.02; 604/6.03; 604/6.07; 604/6.15; 604/408; 604/410; 604/416; 494/23; 494/37; 494/45

(58) Field of Classification Search ............ 604/6.01, 604/6.02, 6.03, 6.04, 6.07, 6.15, 408, 410, 604/416; 436/18; 494/23, 37, 45
See application file for complete search history.

(56) References Cited

U.S. PATENT DOCUMENTS

| 3,847,738 | A | | 11/1974 | Brake et al. |
| 3,921,898 | A | | 11/1975 | Finkel |
| 4,056,484 | A | * | 11/1977 | Heimburger et al. ........... 436/16 |
| 4,120,448 | A | * | 10/1978 | Cullis .............................. 494/43 |
| 4,280,497 | A | * | 7/1981 | Warner et al. ................. 604/408 |
| 4,322,298 | A | * | 3/1982 | Persidsky ....................... 210/787 |
| 4,445,883 | A | * | 5/1984 | Schroendorfer ................ 494/21 |
| 4,482,342 | A | * | 11/1984 | Lueptow et al. ................ 494/21 |
| 4,596,657 | A | * | 6/1986 | Wisdom ......................... 210/206 |
| 4,670,013 | A | * | 6/1987 | Barnes et al. .................. 604/403 |
| 4,806,247 | A | * | 2/1989 | Schoendorfer et al. .. 210/321.68 |
| 4,810,378 | A | * | 3/1989 | Carmen et al. ................ 210/206 |
| 4,834,890 | A | * | 5/1989 | Brown et al. .................. 210/739 |
| 4,919,646 | A | | 4/1990 | Perdriat |
| 4,925,665 | A | * | 5/1990 | Murphy ......................... 424/532 |

(Continued)

OTHER PUBLICATIONS

M. Saljoughian, "Cardioplegic Solution." Accessed Aug. 26, 2007. http://www.uspharmacist.com/oldformat.asp?url=newlook/files/Feat/Cardioplegic.htm&pub.*

(Continued)

Primary Examiner — Leslie Deak
Assistant Examiner — Adam Marcetich

(57) ABSTRACT

This invention is directed to a method of collecting and separating whole blood into components. The method includes the steps of adding an anticoagulant having an acidic pH to a bag for collecting and/or separating whole blood, collecting whole blood in the bag, loading the bag containing anticoagulated whole blood on a rotor, spinning the bag on the rotor to separate the whole blood into at least one component; and squeezing the bag on the rotor to push the component from the separation bag into at least one satellite bag.

17 Claims, 7 Drawing Sheets

U.S. PATENT DOCUMENTS

| | | | |
|---|---|---|---|
| 4,985,153 A * | 1/1991 | Kuroda et al. | 210/782 |
| 5,269,946 A * | 12/1993 | Goldhaber et al. | 210/767 |
| 5,715,731 A | 2/1998 | Koch | |
| 5,879,318 A * | 3/1999 | Van Der Heiden et al. | 604/6.02 |
| 5,885,457 A | 3/1999 | Breillatt, Jr. et al. | |
| 5,928,214 A * | 7/1999 | Rubinstein et al. | 604/410 |
| 6,261,217 B1 | 7/2001 | Unger et al. | |
| 6,277,556 B1 | 8/2001 | Grode et al. | |
| 6,315,706 B1 | 11/2001 | Unger et al. | |
| 6,348,031 B1 | 2/2002 | Unger et al. | |
| 6,447,987 B1 * | 9/2002 | Hess et al. | 435/2 |
| 6,468,732 B1 * | 10/2002 | Malin et al. | 435/2 |
| 6,488,860 B2 * | 12/2002 | Mari et al. | 210/806 |
| 6,495,039 B1 * | 12/2002 | Lee et al. | 210/257.1 |
| 6,773,389 B2 * | 8/2004 | Hlavinka et al. | 494/60 |
| 6,780,333 B1 * | 8/2004 | Brown et al. | 210/789 |
| 6,852,074 B1 | 2/2005 | Jorgensen et al. | |
| 6,910,998 B2 | 6/2005 | Eberle | |
| 7,166,217 B2 * | 1/2007 | Holmes et al. | 210/257.1 |
| 2002/0068674 A1 * | 6/2002 | Hlavinka et al. | 494/37 |
| 2003/0146170 A1 | 8/2003 | Corbin et al. | |
| 2003/0147776 A1 * | 8/2003 | Stroncek et al. | 422/44 |
| 2003/0148256 A1 | 8/2003 | Payrat et al. | |
| 2003/0199573 A1 * | 10/2003 | Druzgala et al. | 514/457 |
| 2004/0104182 A1 | 6/2004 | Holmes et al. | |
| 2004/0147387 A1 * | 7/2004 | Unger et al. | 494/45 |
| 2004/0229204 A1 * | 11/2004 | St. Cyr et al. | 435/2 |
| 2005/0045567 A1 | 3/2005 | Holmes et al. | |

OTHER PUBLICATIONS

U.S. Appl. No. 60/917,794, US Patent Application to Pihlstedt and Holmes, filed May 14, 2007.*

Online encyclopedia article "Acid-citrate-dextrose" accessed Mar. 11, 2010. http://en.wikipedia.org/wiki/Acid-citrate-dextrose.*

Solberg et al, "Centrifugation of very Freshly Donated Blood May Platelets Unstable to Storage in the New Generation of Containers", *Vox Sarig*, 1989:26:25-31.

Solberg, Christel, "Storage of Human Red Blood Cells and Platelets", *Upsala J. Med Sci*, 1988, 93:201-214.

PCT: "International Search Report" with written opinion, PCT/US2007/061301, Feb. 6, 2008.

PCT: "International Preliminary Report on Patentability", Aug. 14, 2008.

* cited by examiner

ADJUSTING PH IN A METHOD OF SEPARATING WHOLE BLOOD

CROSS REFERENCE TO RELATED APPLICATIONS

This application claims benefit under 35 U.S.C. 119(e) of U.S. Provisional Application No. 60/766,586 filed Jan. 30, 2006.

BACKGROUND

For transfusions of blood and blood components, whole blood is typically separated into three components: plasma, red blood cells and platelets.

There are traditionally two ways to obtain these blood components. One way is to collect whole blood from donors/patients and separate it into components manually at some time period after the whole blood collection. Using this method, whole blood is collected into FDA-approved containers that are pyrogen-free and sterile, and contain sufficient anticoagulant for the quantity of blood to be collected. Whole blood which is collected in this way is separated into components manually in a lab by a technician, and separation typically occurs from between about 2 and 8 hours after collection in the United States, and between about 2 to 24 hours in Europe.

Another way to separate whole blood into components is by using apheresis or automated cell-separation devices. Apheresis devices separate whole blood into components automatically, and return any uncollected blood components back to the donor during the collection procedure.

An alternative to manual processing of whole blood as described above is the automatic processing of previously collected whole blood using an automated whole blood processing device such as the Atreus machine, manufactured by Gambro BCT, Inc. (Lakewood, Colo., USA.)

In whole blood processing, (whether by hand or by an automated machine), and in apheresis the addition of anticoagulant to the blood is necessary to prevent the formation of blood clots. In manual whole blood processing, blood is collected from a donor/patient directly into a bag that contains an approved anticoagulant-preservative solution designed to both prevent clotting and maintain cell viability and function during storage. In manual whole blood processing, whole blood is collected in CPD (citrate-phosphate-dextrose) anticoagulant.

In apheresis processing, the anticoagulant ACDA (acid-citrate-dextrose formula A) is added to the blood withdrawn from a donor/patient at the beginning of the collection procedure.

It is to the optimal collection of platelets and to the optimal leukoreduction of red blood cells from whole blood processed on an automated blood processing device that the present invention is directed.

BRIEF SUMMARY OF THE INVENTION

This invention is directed to a method of collecting and separating whole blood into components. The method includes the steps of adding an anticoagulant having an acidic pH to a bag for collecting and/or separating whole blood, collecting whole blood in the bag, loading the bag containing anticoagulated whole blood on a rotor, spinning the bag on the rotor to separate the whole blood into desired components; and squeezing the bag on the rotor to push the desired components from the separation bag into satellite bags.

This invention also includes a method of leukoreducing red blood cells separated from previously collected and stored whole blood. The steps include collecting whole blood in CPD anticoagulant, storing the anticoagulated whole blood overnight, loading the anticoagulated whole blood on a rotor, spinning the rotor to separate the stored whole blood into at least a red blood cell component, and squeezing the blood on the rotor to push at least the red blood cells component into a satellite bag, increasing the pH of the separated red blood cell component in the satellite bag, and leukoreducing the red blood cell component.

DETAILED DESCRIPTION

This invention is for use with automated blood separation devices for separating collected whole blood into components. The whole blood may be separated into components immediately after collection from a donor, or may be separated into components from whole blood which was previously collected from a donor. Previously collected means that the whole blood was collected from a donor at some period of time prior to the blood being separated in the automated blood separation device. The device described below is described in patent application PCT/US2006/031492, herein incorporated by reference in its entirety to the amount not inconsistent.

Figure 1:
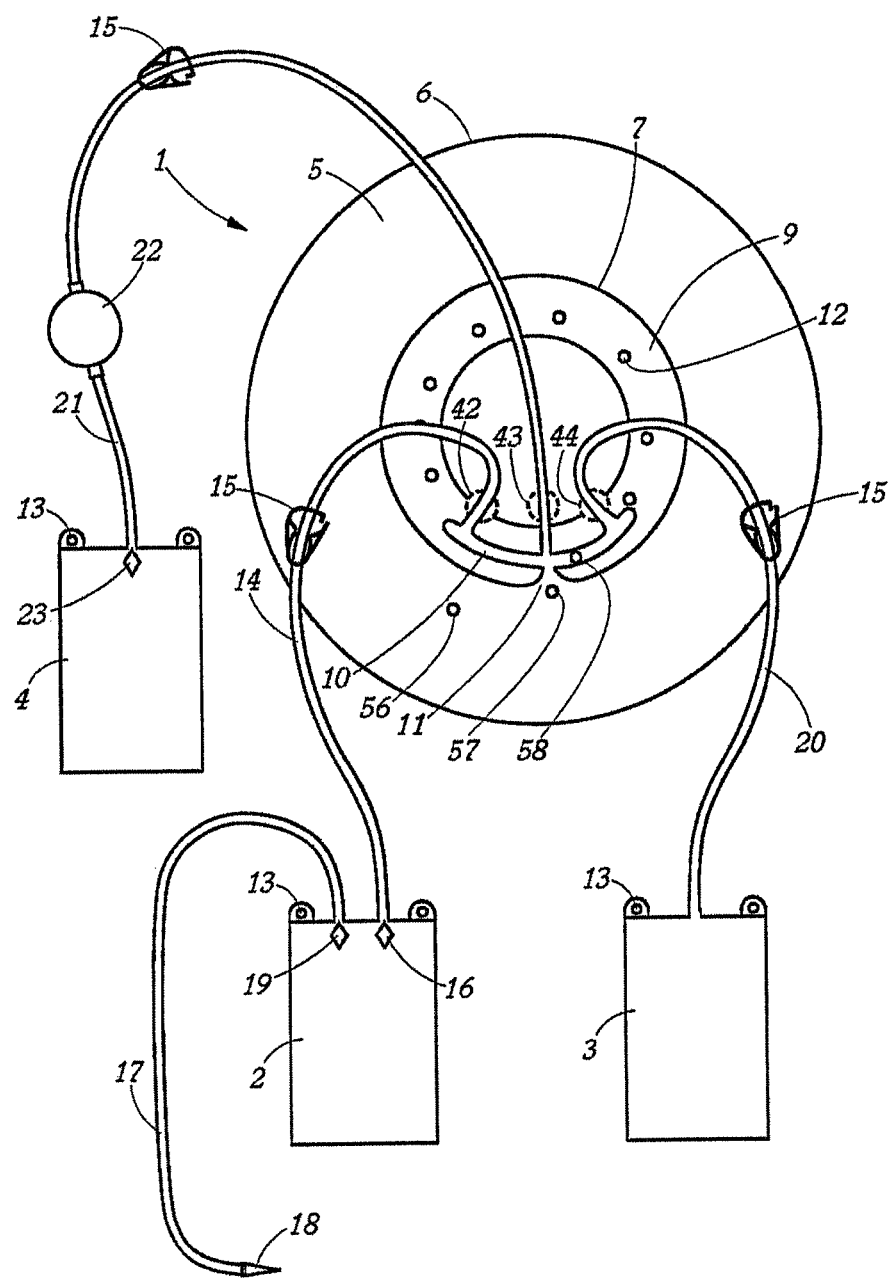
FIG. 1 is a schematic view of a set of separation and collection bags designed for cooperating with an automated whole blood separation apparatus.

FIG. 1 shows an example of a set of bags adapted to the separation of whole blood into a plasma component essentially comprising plasma, a first blood cell component essentially comprising mononuclear cells and platelets, and a second blood cell component essentially comprising red blood cells. This bag set comprises a flexible separation bag 1 and three flexible product bags 2, 3, 4 connected thereto. The separation bag 1 comprises an annular separation chamber 5 having a substantially circular outer edge 6 and an inner circular edge 7. The outer circular edge 6 and the inner circular edge 7 of the separation chamber 5 are substantially concentric. The separation bag 1 further comprises a semi-flexible disk-shaped connecting element 9 that is connected to the inner edge 7 of the annular chamber 5. The disk-shaped connecting element 9 comprises a distribution channel 10 embedded therein, which communicates through a passage 11 with the annular chamber 5. The distribution channel 10 substantially extends along an arc of circle. The disk-shaped connecting element 9 comprises a series of holes 12 for securing the separation bag 1 to the rotor of a centrifuge.

The first satellite bag 2 has two purposes and is successively used as both a blood collection bag and as a mononuclear cell/platelet component bag. The first satellite bag is intended for initially receiving a volume of whole blood from a donor (usually about 450 ml) before the separation process, and the mononuclear cell/platelet component during the separation process. The first satellite bag 2 is flat, substantially rectangular, and comprises two reinforced ears at its upper corners having holes 13 for hanging the bag. It is connected to the separation bag 1 by a first transfer tube 14, fitted with a clamp 15. The first transfer tube 14 has a first end connected to the upper edge of the first satellite bag 2 and a second end connected to a first end of the distribution channel 10.

Anticoagulant is added to the first satellite bag 2. Typically about 63 ml of anticoagulant solution is added to a blood donation of about 450 ml. The anticoagulant may be added to the first satellite bag 2 before the blood is added, or may be added after the blood is added. A plug 16 removable from within the first satellite bag 2 (so-called "frangible pin", for example) blocks a liquid flow through the first transfer tube 14 and prevents the anticoagulant solution from flowing from the first satellite bag 2 into the separation bag 1.

A collection tube 17 is connected at one end to the upper edge of the first satellite bag 2 and comprises, at the other end, a needle protected by a sheath 18. A frangible pin 19 removable from within the first satellite bag 2 plugs the downstream end of the collection tube 17 and prevents the anticoagulant solution from flowing out of the first satellite bag 2 through the collection tube 17.

The second satellite bag 3 is intended for receiving a plasma component. It is flat, substantially rectangular, and comprises two reinforced ears at its upper corners having holes 13 for hanging the bag. It is connected by a second transfer tube 20 to the separation bag 1. The second transfer tube 20, which is fitted with a clamp 15, has a first end connected to the upper edge of the second satellite bag 3 and a second end connected to a second end of the distribution channel 10.

The third satellite bag 4 is intended for receiving a red blood cell component. It is flat, substantially rectangular, and comprises two reinforced ears at its upper corners having holes 13 for hanging the bag. It is connected by a third transfer tube 21 to the separation bag 1. The third transfer tube 21 has a first end connected to the upper edge of the third satellite bag 4 and a second end that is connected to the distribution channel 10 so as to face the passage 11 between the distribution channel 10 and the separation chamber 5. It comprises two segments respectively connected to the inlet and the outlet of a leuko-reduction filter 22. The tube segment connected to the separation bag 1 is fitted with a clamp 15. The filter 22 may be, for example, a filter of the type RC2D manufactured by Pall Corporation. Such a filter comprises a disk-shaped casing to which radial inlet and outlet ports are connected, in diametric opposition. The third satellite bag 4 contains a volume of storage solution for red blood cells. The storage solution may be added to the third satellite bag 4 either before the cells are added or after the cells are added. A plug 23 removable from within the third satellite bag 4 (so-called "frangible pin", for example) blocks a liquid flow through the third transfer tube 21 and prevents the storage solution from flowing from the third satellite bag 4 into the separation bag 1.

Figure 2:
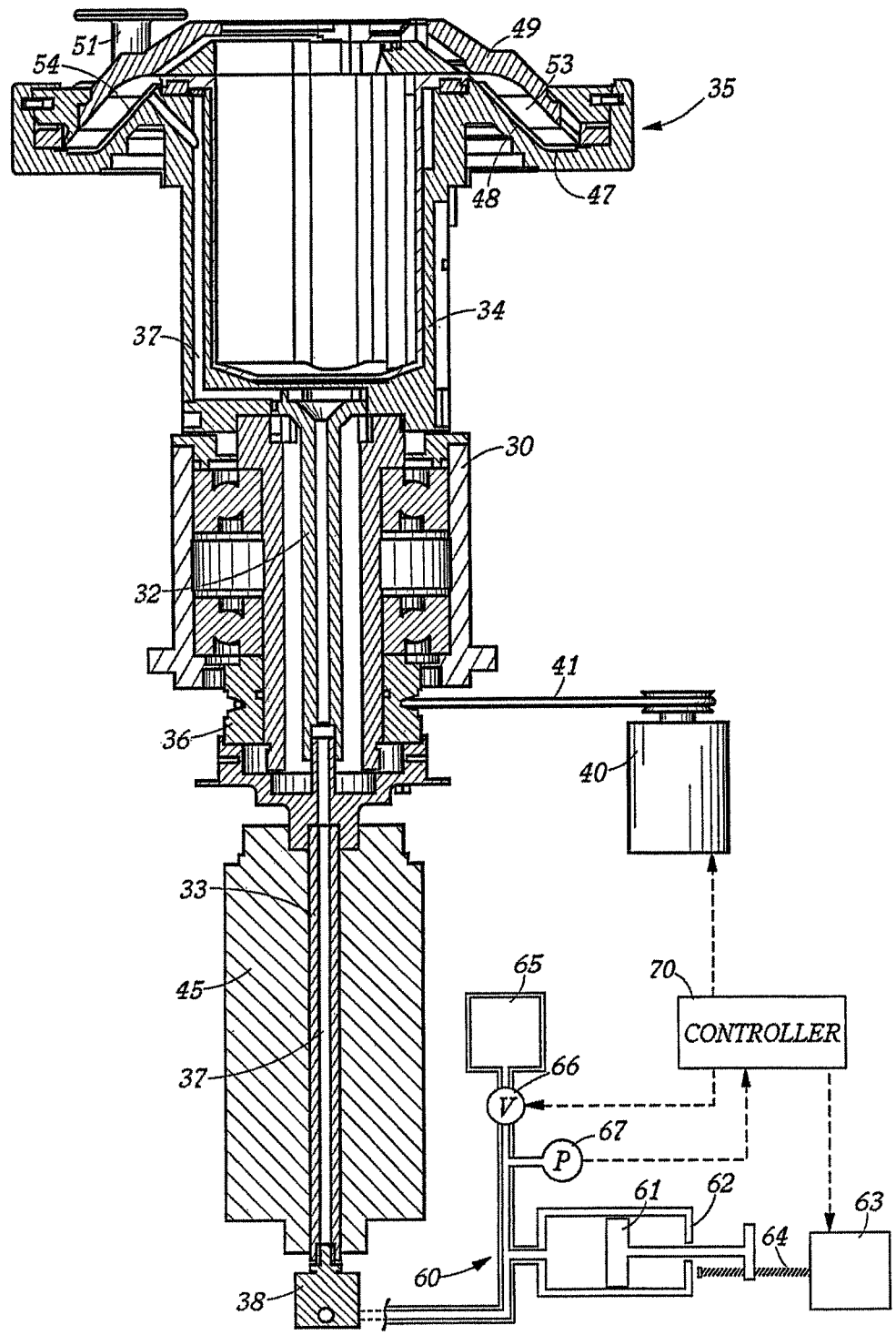
FIG. 2 is a schematic view, partly in cross-section, of a whole blood separation apparatus which may be used with the present invention.
Figure 3:
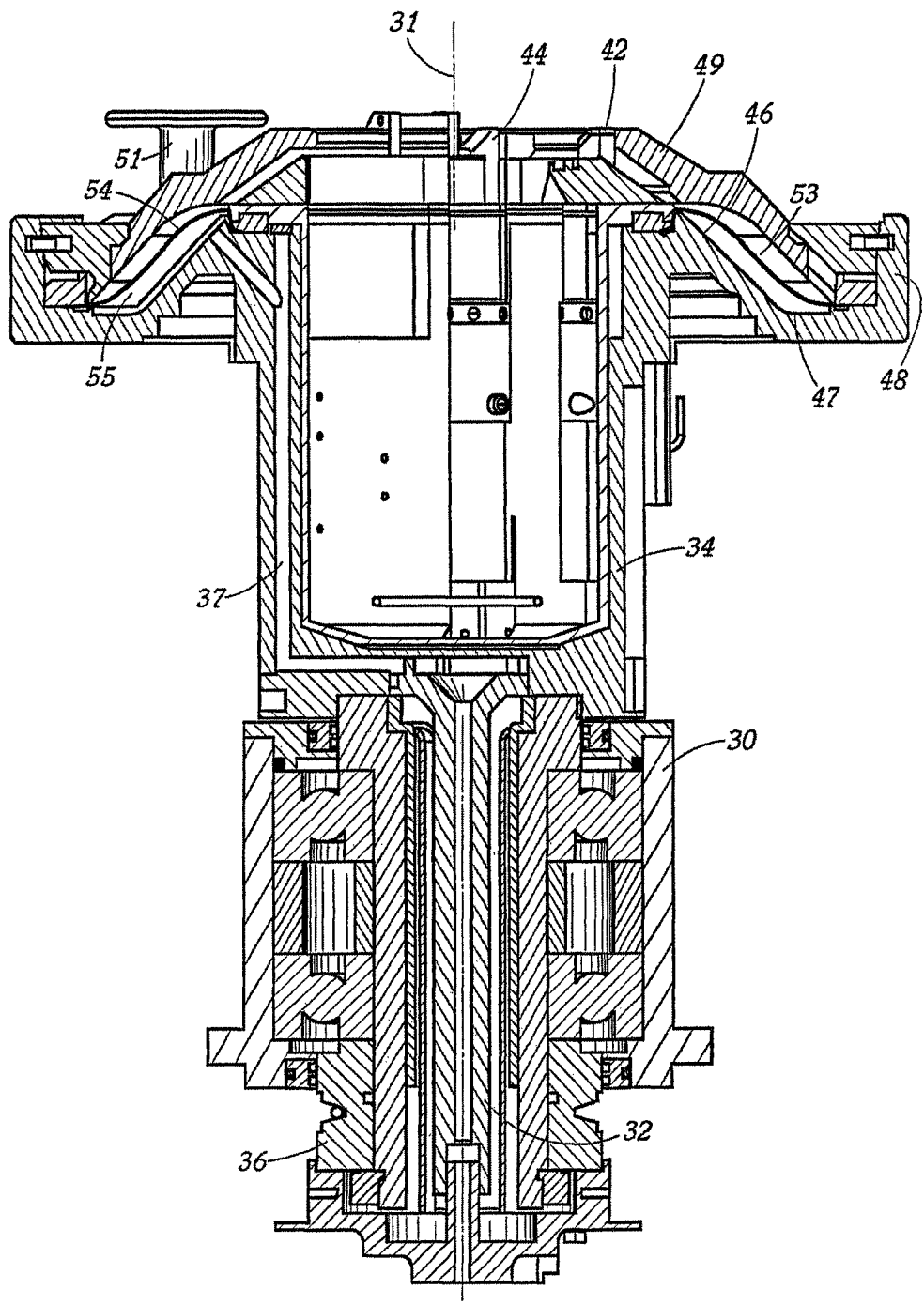
FIG. 3 is a schematic view, partly in cross-section, of a whole blood separation apparatus which may be used with the present invention.

FIGS. 2 and 3 show an embodiment of an apparatus for separating a volume of composite liquid by centrifugation. The apparatus comprises a centrifuge adapted for receiving the separation bags shown in figures, and a component transferring means for causing the transfer of separated components into the satellite bags.

The centrifuge comprises a rotor that is supported by a bearing assembly 30 allowing the rotor to rotate about a vertical central axis 31. The rotor comprises:
 a cylindrical rotor shaft 32, 33;
 a central compartment 34 for containing satellite bags, which is connected to the rotor shaft 32, 33 at the upper end thereof;
 a support member 7 (not shown in FIGS. 3 and 4) for supporting at least one satellite bag in a determined position within the central compartment 34; and
 a circular turntable 35 for supporting a separation bag, which is connected to the compartment 34 at the upper end thereof, the central axes of the rotor shaft 31, 32, the compartment 34 and the turntable 35 coinciding with the rotation axis 31.

The rotor shaft comprises a first upper portion 32 and a second lower portion 33. The upper portion 32 of the shaft extends in part through the bearing assembly 30. A pulley 36 is connected to the lower end of the upper portion 32 of the shaft.

The centrifuge further comprises a motor 40 coupled to the rotor by a belt 41 engaged in a groove of the pulley 36 so as to rotate the rotor about the central vertical axis 31.

The separation apparatus further comprises a first, second and third pinch valve members 42, 43, 44 (see FIG. 1) that are mounted on the rotor for selectively blocking or allowing a flow of liquid through a flexible plastic tube, and selectively sealing and cutting a plastic tube. Each pinch valve member 42, 43, 44 comprises an elongated cylindrical body and a head having a groove that is defined by a stationary upper jaw and a lower jaw movable between an open and a closed position, the groove being dimensioned so that one of the transfer tubes 14, 20, 21 of the bag set shown in FIG. 1 can be snuggly engaged therein when the lower jaw is in the open position. The elongated body contains a mechanism for moving the lower jaw and it is connected to a radio frequency generator that supplies the energy necessary for sealing and cutting a plastic tube. The pinch valve members 42, 43, 44 are mounted at the periphery of the central compartment 34 so that their longitudinal axes are parallel to the central axis 31 of the rotor and their heads protrude above the rim of the compartment 34. The position of the pinch valve members 42, 43, 44 with respect to the separation bag 1 and the transfer tubes 14, 20 connected thereto when the separation bag 1 is mounted on the turntable 35 is shown in dotted lines in FIG. 1. Electric power is supplied to the pinch valve members 42, 43, 44 through a slip ring array 45 that is mounted around the lower portion 33 of the rotor shaft.

The turntable 35 comprises a central frusto-conical portion 46, the upper, smaller edge of which is connected to the rim of the compartment 34, an annular flat portion 47 connected to the lower, larger edge of the frusto-conical portion 46, and an outer cylindrical flange 48 extending upwards from the outer periphery of the annular portion 47. The turntable 35 further comprises a vaulted circular lid 49 that is secured to the flange 48 by a hinge so as to pivot between an open and a closed position. The lid 49 is fitted with a lock 51 by which it can be blocked in the closed position. The lid 49 comprises a large cut-out in its upper part that gives access to the central compartment 34 of the rotor. The lid 49 has an annular interior surface that is so shaped that, when the lid 49 is in the closed position, it defines with the frusto-conical portion 46 and the annular flat portion 47 of the turntable 38 a frusto-conical annular compartment 53 having a radial cross-section that has substantially the shape of a parallelogram. The frusto-conical annular compartment 53, later the "separation compartment", is intended for containing the separation bag 1.

The component transferring means comprises a squeezing system for squeezing the separation bag within the separation compartment 53 and causing the transfer of separated components into the satellite bags. The squeezing system comprises a flexible annular diaphragm 54 that is so shaped as to line the frusto-conical portion 46 and the annular flat portion 47 of the turntable 35, to which it is secured along its smaller and larger circular edges. The squeezing system further comprises a hydraulic pumping station 60 for pumping a hydraulic liquid in and out an expandable hydraulic chamber 55 defined between the flexible diaphragm 54 and the turntable 35, via a duct 37 extending through the rotor from the lower end of the lower portion 33 of the rotor shaft to the turntable 35. The pumping station 60 comprises a piston pump having a piston 61 movable in a hydraulic cylinder 62 fluidly connected via a rotary fluid coupling 38 to the rotor duct 37. The piston 61 is actuated by a stepper motor 63 that moves a lead screw 64 linked to the piston rod. The hydraulic cylinder 62 is also connected to a hydraulic liquid reservoir 65 having an access controlled by a valve 66 for selectively allowing the introduction or the withdrawal of hydraulic liquid into and from a hydraulic circuit including the hydraulic cylinder 62, the rotor duct 37 and the expandable hydraulic chamber 55. A pressure gauge 67 is connected to the hydraulic circuit for measuring the hydraulic pressure therein.

The separation apparatus further comprises three sensors 56, 57, 58 for detecting characteristics of the separation process occurring within a separation bag when the apparatus operates. The three sensors 56, 57, 58 are embedded in the lid 49 at different distances from the rotation axis of the rotor, a first sensor 56 being the farthest to the rotation axis, a third sensor 58 being the closest to the rotation axis and a second sensor 57 occupying an intermediate position. When the lid 49 is closed, the three sensors 56, 57, 58 face the separation bag 1 as shown in FIG. 1. The first sensor 56 (later the "bag sensor") is embedded in the lid 49 so as to be positioned over the separation chamber 5, at about one third of the width of the separation chamber from the inner edge 6 thereof, and it is offset with respect to the passage 11 between the separation chamber 5 and the distribution channel 10. The bag sensor 56 is able to detect the presence or absence of a liquid in the separation chamber 5, as well as red blood cells in a liquid. The second sensor 57 (later the "bay sensor") is embedded in the lid 49 so as to be positioned over the passage 11 between the separation chamber 5 and the distribution channel 10. The bay sensor 57 is in the pathway of any component flowing from the separation chamber 5 into the three satellite bags 2, 3, 4. The bay sensor 57 is able to detect the presence or absence of a liquid in the distribution channel 10 as well as to detect red blood cells in a liquid. The third sensor 58 (later the "channel sensor") is embedded in the lid 49 so as to be positioned over the distribution channel 10. The channel sensor 58 is in the pathway of any component flowing from the separation chamber 5 into the second satellite bag 3. The channel sensor 58 is able to detect the presence or absence of a liquid in the distribution channel 10 as well as to detect red blood cells in a liquid. Each sensor 56, 57, 58 can comprise a photocell including an infra-red LED and a photo-detector. Electric power is supplied to the sensors 56, 57, 58 through the slip ring array 45.

The separation apparatus further comprises a controller 70 including a control unit (microprocessor) and a memory for providing the microprocessor with information and programmed instructions relative to various separation protocols and to the operation of the apparatus in accordance with such separation protocols. In particular, the microprocessor is programmed for receiving information relative to the centrifugation speed(s) at which the rotor is to be rotated during the various stages of a separation process, and information relative to the various transfer flow rates at which separated components are to be transferred from the separation bag 1 into the satellite bags 2, 3, 4. The information relative to the various transfer flow rates can be expressed, for example, as hydraulic liquid flow rates in the hydraulic circuit, or as rotation speeds of the stepper motor 63 of the hydraulic pumping station 60. The microprocessor is further programmed for receiving, directly or through the memory, information from the pressure gauge 67 and from the photocells 56, 57, 58 and for controlling the centrifuge motor 40, the stepper motor 63, and the pinch valve members 42, 43, 44 so as to cause the separation apparatus to operate along a selected separation protocol.

An example of a first separation protocol aimed at the preparation of three blood components, namely a plasma component, a first blood cell component essentially comprising platelets, and a second blood cell component essentially comprising red blood cells, is explained below. This first separation protocol does not require the use of the channel sensor 58. The operation of the separation apparatus along the first separation protocol is as follows:

In the first separation stage, a bag set as shown in FIG. 1, in which a satellite bag contains a volume of whole blood, is set in place in the rotor of a centrifuge (as shown in FIGS. 2, 3).

At the onset of the first stage, the first satellite bag 2 of the bag set of FIG. 1 contains a volume of anticoagulated whole blood (usually about 500 ml). The collection tube 17 has been sealed and cut. The clamps 15 on the transfer tubes 14, 20, 21 connecting the satellite bags 2, 3, 4 to the separation bag 1 are closed. The frangible pin 16 blocking communication between the first satellite bag 2 and the separation bag 1 is broken as well as the frangible pin 23 blocking communication between the third satellite bag 4 and the separation bag 1. The first satellite bag 2 and the third satellite bags 4 are engaged on the first couple of pegs of a bag holder (not shown), the first satellite bag 2 being engaged first. The second satellite bag 3 is engaged on the second couple of pegs (not shown). The bag holder is mounted in a cradle (not shown), as a result of which the first satellite bag 2 is adjacent to the inner surface of the cradle. The cradle is then fully inserted into the central compartment 34 of the centrifuge. The satellite bags 2, 3, 4 are then substantially located on one side of a plane containing the rotation axis of the rotor 31. The collection bag 1 is laid on the turntable 35 and the pins on the flange of the rotor liner are engaged in the holes 12 of the disk-shaped connecting element 9 of the separation bag 1. The first transfer tube 14 connecting the first satellite bag 2 to the separation bag 1 is engaged in the first pinch valve member 42, the second transfer tube 20 connecting the second satellite bag 3 to the separation bag 1 is engaged in the third pinch valve member 44, and the third transfer tube 21 connecting the third satellite bag 4 to the separation bag 1 is engaged in the second pinch valve member 43. The clamps 15 on the transfer tubes 14, 20, 21 connecting the satellite bags 2, 3, 4 to the separation bag 1 are opened. The lid 49 of the rotor is closed.

In the second stage, the anticoagulated whole blood contained in the first satellite bag 2 is transferred into the separation bag 1.

At the onset of the second stage, the first pinch valve member 42 is open and the second and third pinch valve members 43, 44 are closed. The rotor is set in motion by the centrifuge motor 40 and its rotation speed increases steadily until it reaches a first centrifugation speed (e.g. about 1500 RPM) that is so selected as:

To be high enough to cause the transfer, under centrifugation forces, of the content of the first satellite bag 2 into the separation bag 1;

To be high enough to cause the whole transfer to happen in the shorter period of time; while, at the same time, To be low enough not to cause pressure within the first satellite bag 2 to substantially exceed a determined pressure threshold above which hemolysis would occur;

To be low enough not to generate shearing forces in the flow of blood entering the separation bag 1 that would cause hemolysis.

It has been determined that the pressure threshold above which hemolysis occurs in the satellite bag 2 is about 10 PSI, and that the maximum rotation speed at which such pressure threshold is not reached and the shearing forces in the blood flow entering the separation bag do not cause hemolysis is about 1800 RPM. At a rotation speed of about 1500 RPM, it takes about one minute for transferring about 500 ml of anticoagulated blood from the satellite bag 2 into the separation bag 1.

If the bag cell 56 has not detected red blood cell within a predetermined period of time following the start of the centrifugation process, the control unit 70 causes the rotor to stop and an alarm to be emitted. This could happen in particular if the frangible pin 16 has not been broken or if the clamp 15 on the first transfer tube 14 has not been opened.

In the third stage, the blood within the separation chamber is sedimented to a desired level.

At the onset of this stage, the pinch valve members 42, 43, 44 are closed. The rotor is rotated at a second, high centrifugation speed (for example, about 3200 RPM) for a predetermined period of time (for example, about 220 seconds) that is selected so that, whatever the hematocrit of the whole blood initially transferred in the separation bag 1, the blood sediments therein at the end of the predetermined period to a point where the hematocrit of the outer annular red blood cell layer is about 90 and the inner annular plasma layer is substantially devoid of cells. In more details, at the outcome of this sedimentation stage, the separation bag 1 exhibits four layers: a first inner layer mainly comprising plasma, a second intermediate layer mainly comprising platelets, a third intermediate layer mainly comprising mononuclear cells (lymphocytes and monocytes), and a fourth outer layer mainly comprising red blood cells (granulocytes remain embedded in the most inner layer of red blood cells).

In the forth stage, a plasma component is transferred into the second satellite bag 3.

At the onset of this stage, the pinch valve members 42, 43, 44 are closed. The rotor is rotated at the same high centrifugation speed as in the sedimentation stage. After a predetermined period of time after the bag sensor 56 has stopped detecting red blood cells, which can happen before the end of the predetermined sedimentation period, the third pinch valve member 44 controlling the access to the second satellite bag 3 is opened and the pumping station 60 is actuated so as to pump hydraulic liquid at a constant flow rate (for example, about 220 ml/min) into the hydraulic chamber 55. The expanding hydraulic chamber 55 squeezes the separation bag 1 and causes the transfer of plasma into the second satellite bag 3. The pumping station 60 is stopped and the third pinch valve member 44 is closed after a predetermined period of time has elapsed following the detection of red blood cells by the bay sensor 57. A small volume of plasma (for example, about 5 ml) remains in the separation bag 1.

The transfer flow rate of the plasma component (which is directly related to the flow rate of the hydraulic fluid) is selected to be as high as possible without disturbing the platelet layer so as to avoid contaminating the plasma component with platelets.

In the fifth stage a platelet/mononuclear cell component is transferred into the first satellite bag 2.

The fifth stage can start as soon as the third pinch valve member 44 is closed at the end of the fourth stage. At the onset of this fifth stage, the pinch valve members 42, 43, 44 are closed. The rotor is rotated at the same high centrifugation speed as previously. The first pinch valve member 42 controlling the access to the first satellite bag 2 is opened and the pumping station 60 is actuated so as to pump hydraulic liquid at a constant flow rate (for example, about 140 ml/min) into the hydraulic chamber 55. The expanding hydraulic chamber 55 squeezes the separation bag 1 and causes the transfer, into the first satellite bag 2, of a platelet/mononuclear cell component comprising the residual volume of plasma, the platelets, lymphocytes, monocytes and a small amount of red blood cells. The pumping station 60 is stopped and the first pinch valve member 42 is closed after a predetermined volume has been transferred into the first satellite bag 2, that is also after a predetermined amount of time has elapsed for a given hydraulic liquid flow rate. This predetermined volume of platelet/mononuclear cell component depends in part on the residual amount of plasma in the separation bag 1 at the end of the fourth stage. For example, when the residual volume of plasma in the separation bag 1 is determined by the bay sensor 57, the predetermined volume of the platelet/mononuclear cell component can be set at about between 10 and 15 ml, including about 5 ml of plasma and about 5 ml of red bloods cells.

In the sixth stage the storage solution for red blood cells contained in the third satellite bag 4 is transferred into the separation bag 1.

The sixth stage can start as soon as the third pinch valve member 42 is closed at the end of the fifth stage. At the onset of this fifth stage, the pinch valve members 42, 43, 44 are closed. The rotor is rotated at the same high centrifugation speed as previously. The second pinch valve member 43 controlling the access to the third satellite bag 4 is opened, allowing the storage solution contained in the third satellite bag 4 to flow, under centrifugation forces, from the third satellite bag 4 into the separation bag 1, through the filter 22. After a predetermined period of time has elapsed after the opening of the second pinch valve member 43, the rotor is sharply braked so that its rotation speed decreases rapidly to a third, reduced speed (for example, 1500 RPM), so as to cause a suspension of the red blood cells contained in the separation bag in the storage solution and lower the viscosity thereof.

In the seventh stage a red blood cell component is transferred into the third satellite bag 4.

The seventh stage can start after a predetermined period of time has elapsed after the rotor rotates at the third rotation speed. At the onset of this stage the second pinch valve member 43 controlling the access to the third satellite bag 4 is open and the pinch valve members 42, 44 are closed. The rotor rotates at the third rotation speed. The pumping station 60 is actuated so as to pump hydraulic liquid at a first flow rate into the hydraulic chamber 55 and consequently squeeze the separation bag 1 so as to cause the transfer, through the filter 22, of a red blood cell component into the third satellite bag 4. The first transfer flow rate of the red blood cell component (which is directly related to the flow rate of the hydraulic fluid) is selected to be as high as possible without damaging the red blood cells (hemolysis). When the pressure of the hydraulic liquid measured by the pressure gauge 67 reaches a first high pressure threshold, the flow rate of the hydraulic liquid is decreased from the first flow rate to a second flow rate. When the pressure of the hydraulic liquid measured by the pressure gauge 67 reaches a second high pressure threshold, the flow rate of the hydraulic liquid is further decreased from the second flow rate to a third flow rate. The second and third transfer flow rates of the red blood cell component are selected so that a maximal portion of the red blood cell component is transferred into the third satellite bag 4. The white blood cells (granulocytes and residual monocytes and lymphocytes) are trapped by the filter 22, so that the ultimate packed red blood cell component in the third satellite bag 4 is substantially devoid of white blood cells.

In the eighth stage the centrifugation process is ended.

When a predetermined period of time (for example, about 30 seconds) has elapsed after the pressure of the hydraulic liquid has reached the second pressure threshold, the rotation speed of the rotor is decreased until the rotor stops, the pumping station 60 is actuated so as to pump the hydraulic liquid from the hydraulic chamber 55 at a high flow rate (for example, about 800 ml/min) until it the hydraulic chamber 55 is empty, and the three pinch valve members 42, 43, 44 are actuated so as to seal and cut the tubes 14, 20, 21.

Another automatic whole blood processing system with which the present invention can be used is shown in FIGS. 4 through 7. This automatic whole blood processing system is described in patent application PCT/US2006/21827, herein incorporated by reference in its entirety to the amount not inconsistent.

Figure 4:
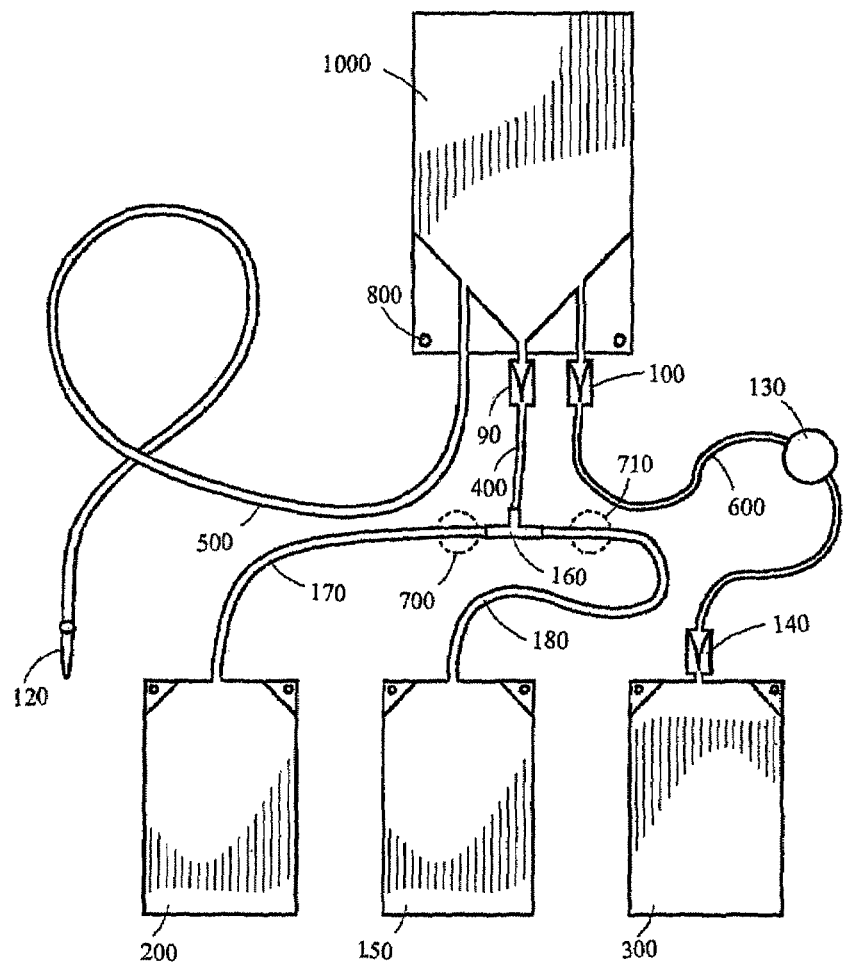
FIG. 4 is a schematic view of another set of separation and collection bags designed for cooperating with another automated whole blood separation apparatus.

FIG. 4 shows an example of a set of bags adapted to the separation of a composite liquid (e.g. whole blood) into a first component (e.g. a plasma component), an intermediate component (e.g. a platelet component), and a second component (e.g. a red blood cell component). This bag set comprises a flexible separation bag 1000 and three flexible satellite bags 200, 300, 150 connected thereto.

When the composite liquid is whole blood, the separation bag 1000 has two purposes, and is successively used as a collection bag and as a separation bag. It is intended for initially receiving a discrete volume of whole blood from a donor (usually about 450 ml) and to be used later as a separation chamber in a separation apparatus. The separation bag 1000 is flat and generally rectangular. It is made of two rectangular sheets of plastic material that are welded together so as to define therebetween an interior space having a main rectangular portion connected to a triangular top downstream portion. A first tube 400 is connected to the tip of the triangular portion, and a second and a third tubes 500, 600 are connected to either lateral edges of the triangular portion, respectively. The proximal ends of the three tubes 400, 500, 600 are embedded between the two sheets of plastic material so as to be parallel. The separation bag 1000 further comprises a hole 800 in each of its corners that are adjacent to the three tubes 400, 500, 600. The holes 800 are used to secure the separation bag to a separation cell, as will be described later.

A volume of anticoagulant (typically about 63 ml for a blood donation of about 450 ml) is initially added to the separation bag, and the first and third tubes 400, 600 are fitted at their proximal end with a breakable stopper 90, 100 respectively, blocking a liquid flow therethrough.

The second tube 500 is a collection tube having a needle 120 connected to its distal end. At the beginning of a blood donation, the needle 120 is inserted in the vein of a donor and blood flows into the collection (separation) bag 1000. After a desired volume of blood has been collected in the collection (separation) bag 1000, the collection tube 500 is sealed and cut.

The first satellite bag 200 is intended for receiving a plasma component. It is flat and substantially rectangular. It is connected to the distal end of the first tube 400.

The second satellite bag 300 is intended for receiving a red blood cell component. It is flat and substantially rectangular. It is connected to the distal end of the third tube 600. The third tube 600 comprises two segments respectively connected to the inlet and the outlet of a leukoreduction filter 130. The second satellite bag 300 contains a volume of storage solution for red blood cells, and the third tube 600 is fitted at its distal end with a breakable stopper 140 blocking a liquid flow therethrough.

The third satellite bag 150 is intended to receive a platelet component. Like the first and second satellite bags 200, 300, the third satellite bag 150 is flat and substantially rectangular.

The bag set also contains a T-shaped three-way connector 160 having its leg connected by the first tube 400 to the separation bag 1000, a first arm connected by a fourth tube 170 to the first satellite bag 200 (plasma component bag), and a second arm connected by a fifth tube 180 to the third satellite bag 150 (platelet component bag).

Figure 5:
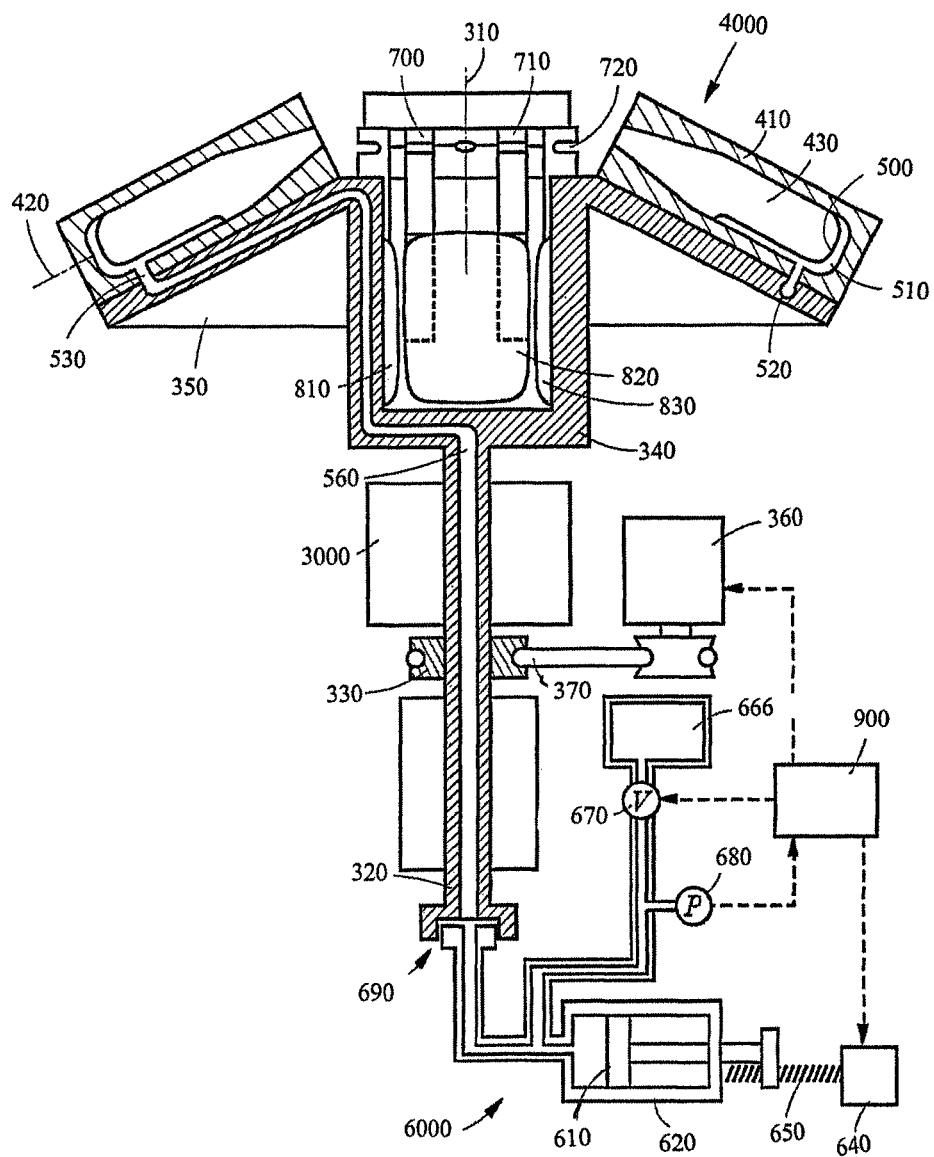
FIG. 5 is a schematic view, partly in cross-section, of a whole blood separation apparatus which may be used with the present invention.
Figure 6:
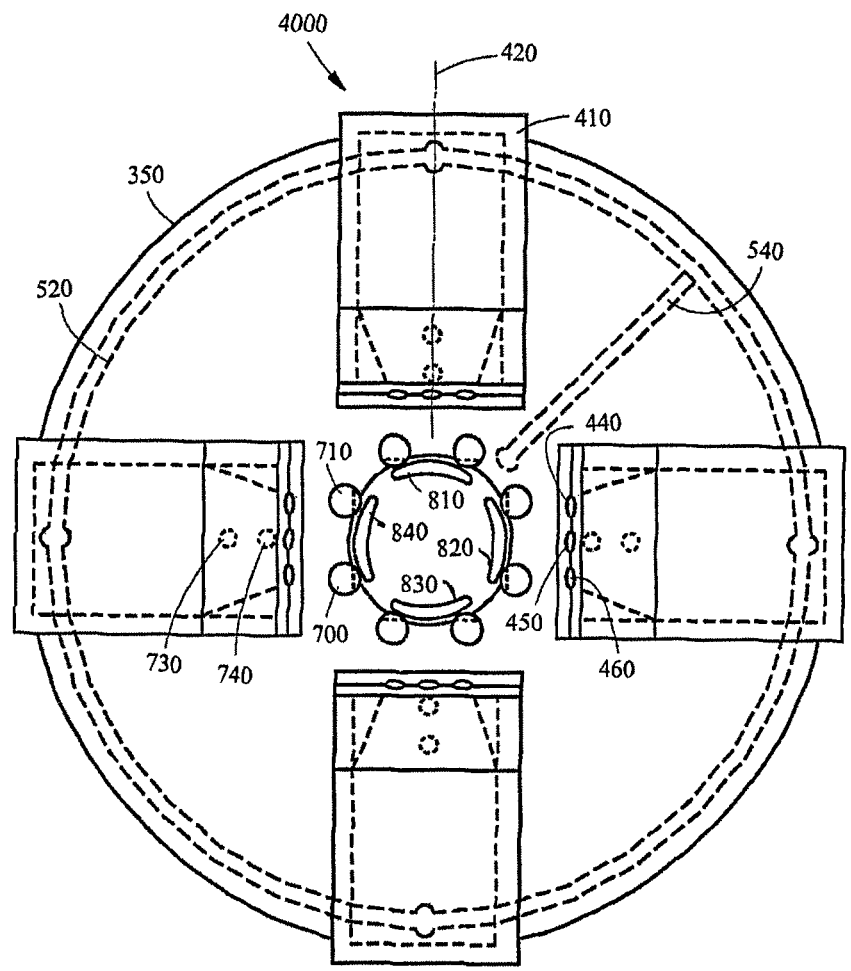
FIG. 6 is a top view of the rotor of the separation apparatus of FIG. 5.
Figure 7:
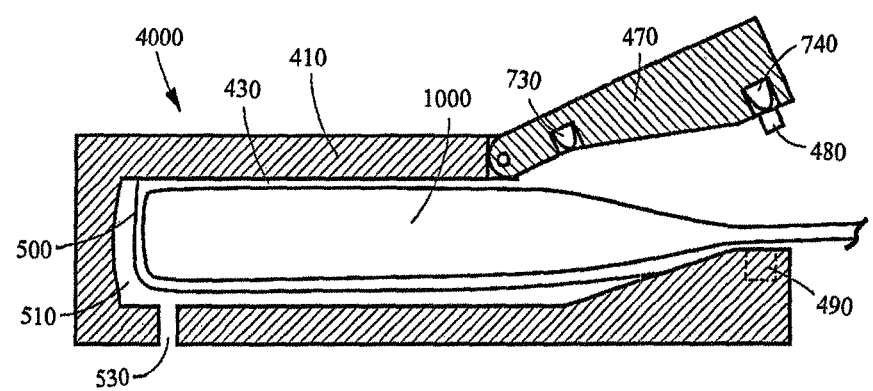
FIG. 7 in schematic view, in cross-section along a radial plane, of a separation cell of the separation apparatus of FIGS. 5-7.

FIGS. 5, 6, 7 show a first embodiment of an apparatus for simultaneously separating by centrifugation four discrete volumes of a composite liquid. The apparatus comprises:
  a centrifuge adapted to receive four bag sets shown in FIG. 4, with the four discrete volumes of a composite liquid contained in the four separation bags;
  a component transferring means for transferring at least one separated component from each separation bag into a satellite bag connected thereto;
  a first balancing means for initially balancing the rotor when the weights of the four separation bags are different; and
  a second balancing means for balancing the rotor when the weights of the separated components transferred into the satellite bags cause an unbalance of the rotor.

The centrifuge comprises a rotor that is supported by a bearing assembly 3000 allowing the rotor to rotate around a rotation axis 310. The rotor comprises:
  a cylindrical rotor shaft 320 to which a pulley 330 is connected;
  a storage means comprising a central cylindrical container 340 for containing satellite bags, which is connected to the rotor shaft 320 at the upper end thereof so that the longitudinal axis of the rotor shaft 320 and the longitudinal axis of the container 340 coincide with the rotation axis 310, and
  a frusto-conical turntable 350 connected to the upper part of the central container 340 so that its central axis coincides with the rotation axis 310. The frusto-conical turntable 350 flares underneath the opening of the container 340. Four identical separation cells 4000 are mounted on the turntable 350 so as to form a symmetrical arrangement with respect to the rotation axis 310.

The centrifuge further comprises a motor 360 coupled to the rotor by a belt 370 engaged in a groove of the pulley 330 so as to rotate the rotor about the rotation axis 310.

Each separation cell 4000 comprises a container 410 having the general shape of a rectangular parallelepiped. The separation cells 4000 are mounted on the turntable 350 so that their respective median longitudinal axes 420 intersect the rotation axis 310, so that they are located substantially at the same distance from the rotation axis 310, and so that the angles between their median longitudinal axes 420 are substantially the same (i.e. 90 degrees). The exact position of the separation cells 4000 on the turntable 350 is adjusted so that the weight on the turntable is equally distributed when the separation cells 4000 are empty, i.e. so that the rotor is balanced. It results from the arrangement of the separating cells 4000 on the turntable 350 that the separating cells 4000 are inclined with respect to the rotation axis 310 of an acute angle equal to the angle of the frustum of a cone that geometrically defines the turntable 350.

Each container 410 comprises a cavity 430 that is so shaped and dimensioned as to loosely accommodate a separation bag 1000 full of liquid, of the type shown in FIG. 4. The cavity 430 (which will be referred to later also as the "separation compartment") is defined by a bottom wall, that is the farthest to the rotation axis 310, a lower wall that is the closest to the turntable 350, an upper wall opposite to the lower wall, and two lateral walls. The cavity 430 comprises a main part, extending from the bottom wall, which has substantially the shape of a rectangular parallelepiped with rounded angles, and an upper part, which has substantially the shape of a prism having convergent triangular bases. In other words, the upper part of the cavity 430 is defined by two couples of opposite walls converging towards the central median axis 420 of the cavity 430.

One interest of this design is to cause a radial dilatation of the thin layer of a minor component of a composite fluid (e.g. the platelets in whole blood) after separation by centrifugation, and makes it more easily detectable in the upper part of a separation bag. As shown in FIG. 5, the two couples of opposite walls of the upper part of the separation cell 4000 converge towards three cylindrical parallel channels 440, 450, 460, opening at the top of the container 410, and in which, when a separation bag 1000 is set in the container 410, the three tubes 400, 500, 600 extend.

The container 410 also comprises a hinged lateral lid 470 (see FIG. 7), which is comprised of an upper portion of the external wall of the container 410, i.e. the wall that is opposite to the turntable 350. The lid 470 is so dimensioned as to allow, when open, an easy loading of a separation bag 1000 full of liquid into the separation cell 4000. The container 410 comprises a fast locking means (not shown) by which the lid 470 can be locked to the remaining part of the container 410.

The container 410 also comprises a securing means for securing a separation bag 1000 within the separation cell 4000. The bag securing means comprises two pins 480 protruding on the internal surface of the lid 470, close to the top of separation cell 4000, and two corresponding recesses 490 in the upper part of the container 410. The two pins 480 are so spaced apart and dimensioned as to fit into the two holes 800 in the upper corner of a separation bag 1000.

The separation apparatus further comprises a component transferring means for transferring at least one separated component from each separation bag into a satellite bag connected thereto. The component transferring means comprises a squeezing system for squeezing the separation bags 1000 within the separation compartments 430 and causing the transfer of separated components into satellite bags 200, 300, 150.

The squeezing system comprises a flexible diaphragm 500 that is secured to each container 410 so as to define an expandable chamber 510 in the cavity thereof. More specifically, the diaphragm 500 is dimensioned so as to line the bottom wall of the cavity 430 and a large portion of the lower wall of the cavity 430, which is the closest to the turntable 350.

The squeezing system further comprises a peripheral circular manifold 520 that forms a ring within the turntable 350 extending close to the periphery of the turntable 350. Each expansion chamber 510 is connected to the manifold 520 by a supply channel 530 that extends through the wall of the respective container 410, close to the bottom thereof.

The squeezing system further comprises a hydraulic pumping station 6000 for pumping a hydraulic liquid in and out the expandable chambers 510 within the separation cells 4000. The hydraulic liquid is selected so as to have a density slightly higher than the density of the more dense of the components in the composite liquid to be separated (e.g. the red blood cells, when the composite liquid is blood). As a result, during centrifugation, the hydraulic liquid within the expandable chambers 510, whatever the volume thereof, will generally remain in the most external part of the separation cells 4000. The pumping station 6000 is connected to the expandable chambers 510, through a rotary seal 690, by a duct 560 that extends through the rotor shaft 320, the bottom and lateral wall of the central container 340, and, from the rim of the central container 340, radially through the turntable 350 where it connects to the manifold 520.

As shown in FIG. 5, the pumping station 6000 comprises a piston pump having a piston 610 movable in a hydraulic cylinder 620 fluidly connected via a rotary fluid coupling to the rotor duct 540. The piston 610 is actuated by a stepper motor 640 that moves a lead screw 650 linked to the piston rod. The hydraulic cylinder 620 is also connected to a hydraulic liquid reservoir 660 having an access controlled by a valve 670 for selectively allowing the introduction or the withdrawal of hydraulic liquid into and from a hydraulic circuit including the hydraulic cylinder 620, the rotor duct 560 and the expandable hydraulic chambers 510. A pressure gauge 680 is connected to the hydraulic circuit for measuring the hydraulic pressure therein.

The separation apparatus further comprises four pairs of a first and second pinch valve members 700, 710 that are mounted on the rotor around the opening of the central container 340. Each pair of pinch valve members 700, 710 faces one separation cell 4000, with which it is associated. The pinch valve members 700, 710 are designed for selectively blocking or allowing a flow of liquid through a flexible plastic tube, and selectively sealing and cutting a plastic tube. Each pinch valve member 700, 710 comprises an elongated cylindrical body and a head having a groove 720 that is defined by a stationary upper jaw and a lower jaw movable between an open and a closed position. The groove 720 is so dimensioned that one of the tubes 400, 170, 180 of the bag set shown in FIG. 4 can be snuggly engaged therein when the lower jaw is in the open position. The elongated body contains a mechanism for moving the lower jaw and it is connected to a radio frequency generator that supplies the energy necessary for sealing and cutting a plastic tube. The pinch valve members 700, 710 are mounted inside the central container 340, adjacent the interior surface thereof, so that their longitudinal axes are parallel to the rotation axis 310 and their heads protrude above the rim of the container 340. The position of a pair of pinch valve members 700, 710 with respect to a separation bag 1000 and the tubes 400, 170, 180 connected thereto when the separation bag 1000 rests in the separation cell 4000 associated with this pair of pinch valve members 700, 710 is shown in doted lines in FIG. 4. Electric power is supplied to the pinch valve members 700, 710 through a slip ring array that is mounted around a lower portion of the rotor shaft 320.

The separation apparatus further comprises four pairs of sensors 730, 740 (see FIGS. 6 and 7) for monitoring the separation of the various components occurring within each separation bag when the apparatus operates. Each pair of sensors 730, 740 is embedded in the lid 470 of the container 410 of each separation cell 4000 along the median longitudinal axis 420 of the container 410, a first sensor 730 being located the farthest and a second sensor 740 being located the closest to the rotation axis 310. When a separation bag 1000 rests in the container 410 and the lid 470 is closed, the first sensor 730 (later the bag sensor) faces the upper triangular part of the separation bag 1000 and the second sensor 740 (later the tube sensor) faces the proximal end of the first tube 400. The bag sensor 730 is able to detect blood cells in a liquid. The tube sensor 740 is able to detect the presence of absence of liquid in the tube 400 as well as to detect blood cells in a liquid. Each sensor 730, 740 may comprise a photocell including an infrared LED and a photo-detector. Electric power is supplied to the sensors 730, 740 through the slip ring array that is mounted around the lower portion of the rotor shaft 320.

The separation apparatus further comprises a first balancing means for initially balancing the rotor when the weights of the four separation bags 1000 contained in the separation cells 4000 are different. The first balancing means substantially comprises the same structural elements as the elements of the component transferring means described above, namely: four expandable hydraulic chambers 510 interconnected by a peripheral circular manifold 520, and a hydraulic liquid pumping station 6000 for pumping hydraulic liquid into the hydraulic chambers 510 through a rotor duct 560, which is connected to the circular manifold 520. In order to initially balance the rotor, whose four separation cells 4000 contain four discrete volumes of a composite liquid that may not have the same weight (because the four volumes may be not equal, and/or the density of the liquid may slightly differ from one volume to the other one), the pumping station 6000 is controlled so as to pump into the interconnected hydraulic chambers 510, at the onset of a separation process, a predetermined volume of hydraulic liquid that is so selected as to balance the rotor in the most unbalanced situation. For whole blood, the determination of this balancing volume takes into account the maximum difference in volume between two blood donations, and the maximum difference in hematocrit (i.e. in density) between two blood donations. Under centrifugation forces, the hydraulic liquid will distribute unevenly in the four separation cells 4000 depending on the difference in weight of the separation bags 1000, and balance the rotor. In order to get an optimal initial balancing, the volume of the cavity 430 of the separation cells 4000 should be selected so that the cavities 430, whatever the volume of the separation bags 1000 contained therein, are not full after the determined amount of hydraulic liquid has been pumped into the interconnected expansion chambers 510.

The separation apparatus further comprises a second balancing means, for balancing the rotor when the weights of the components transferred into the satellite bags 200, 300, 150 in the central container 340 are different. For example, when two blood donations have the same hematocrit and different volumes, the volumes of plasma extracted from each donation are different, and the same is true when two blood donations have the same volume and different hematocrit. As shown in FIGS. 5 and 6 the second balancing means comprises four flexible rectangular pouches 810, 820, 830, 840 that are interconnected by four tube sections (not shown), each tube section connecting two adjacent pouches by the bottom thereof. The pouches 810, 820, 830, 840 contain a volume of balancing liquid having a density close to the density of the composite liquid. The volume of balancing liquid is so selected as to balance the rotor in the most unbalanced situation. The four pouches 810, 820, 830, 840 are so dimensioned as to line the inner surface of the central container 340 and to have an internal volume that is larger than the volume of balancing liquid so that the balancing liquid can freely expand in any of the pouches 810, 820, 830, 840. In operation, if, for example, four satellite bags 200 respectively adjacent to the four pouches 810, 820, 830, 840 receive different volumes of a plasma component, the four satellite bags 200 will press unevenly, under centrifugation forces, against the four pouches 810, 820, 830, 840, which will result in the balancing liquid becoming unevenly distributed in the four pouches 810, 820, 830, 840 and compensating for the difference in weight in the satellite bags 200.

The separation apparatus further comprises a controller 900 including a control unit (e.g. a microprocessor) and a memory unit for providing the microprocessor with information and programmed instructions relative to various separation protocols (e.g. a protocol for the separation of a plasma component and a blood cell component, or a protocol for the separation of a plasma component, a platelet component, and a red blood cell component) and to the operation of the apparatus in accordance with such separation protocols. In particular, the microprocessor is programmed for receiving information relative to the centrifugation speed(s) at which the rotor is to be rotated during the various stages of a separation process (e.g. stage of component separation, stage of a plasma component expression, stage of suspension of platelets in a plasma fraction, stage of a platelet component expression, etc), and information relative to the various transfer flow rates at which separated components are to be transferred from the separation bag 1000 into the satellite bags 200, 300, 150. The information relative to the various transfer flow rates can be expressed, for example, as hydraulic liquid flow rates in the hydraulic circuit, or as rotation speeds of the stepper motor 640 of the hydraulic pumping station 6000. The microprocessor is further programmed for receiving, directly or through the memory, information from the pressure gauge 680 and from the four pairs of photocells 730, 740 and for controlling the centrifuge motor 360, the stepper motor 640 of the pumping station 6000, and the four pairs of pinch valve members 700, 710 so as to cause the separation apparatus to operate along a selected separation protocol.

According to a first separation protocol, four discrete volumes of blood are separated into a plasma component, a first cell component comprising platelets, white blood cells, some red blood cells and a small volume of plasma (later the "buffy coat" component) and a second cell component mainly comprising red blood cells. Each volume of blood is contained in a separation bag 1000 of a bag set represented in FIG. 4, in which it has previously been collected from a donor using the collection tube 500. After the blood collection, the collection tube 500 has been sealed and cut close to the separation bag. Typically, the volumes of blood are not the same in the four separation bags 1000, and the hematocrit varies from one separation bag 1000 to another one. Consequently, the separation bags 1000 have slightly different weights.

The first stage begins by loading the four bag sets into the four separation cells 4000. The lids 470 are closed and locked, whereby the separation bags 1000 are secured by their upper edge to the containers 410 (the pins 480 of the securing means pass then through the holes 800 in the upper corner of the separation bags 1000 and engage the recesses 490 or the securing means).

The tubes 170 connecting the separations bags 1000 to the plasma component bags 200, through the T connectors 160, are inserted in the groove 720 of the first pinch valve members 700. The tubes 180 connecting the separations bags 1000 to the buffy coat component bags 150, through the T connector 160, are inserted in the groove 720 of the second pinch valve members 710. The four plasma component bags 200, the four buffy coat component bags 150, the four red blood cell component bags 300 and the four leukoreduction filters 130 are inserted in the central compartment 340 of the rotor. The four plasma component bags 200 are respectively placed in direct contact with the pouches 810 to 840 of the second balancing means. The pinch valve members 700, 710 are closed and the breakable stoppers 90 in the tubes 400 connecting the separation bags 1000 to the T connectors 100 are manually broken.

In the second stage, the rotor is balanced in order to compensate for the difference in weights of the separation bags.

At the onset of the second stage, all the pinch valve members 700, 710 are closed. The rotor is set in motion by the centrifuge motor 360 and its rotation speed increases steadily until it rotates at a first centrifugation speed. The pumping station 6000 is actuated so as to pump a predetermined overall volume of hydraulic liquid into the four hydraulic chambers 510, at a constant flow rate. This overall volume of liquid is predetermined taking into account the maximum variation of weight between blood donations, so that, at the end of the second stage, the weights in the various separation cells 400 are substantially equal and the rotor is substantially balanced, whatever the specific weights of the separation bags 1000 that are loaded in the separation cells 4000. Note that this does not imply that the internal cavity 430 of the separation cells 4000 should be filled up at the end of the balancing stage. For the purpose of balancing the rotor, it suffices that there is enough hydraulic liquid in the separation cells 4000 for equalizing the weights therein, and it does not matter if an empty space remains in each separation cell 4000 (the size of this empty space essentially depends on the volume of the internal cavity 430 of a separation cell 4000 and the average volume of a blood donation). Because the hydraulic chambers 510 are interconnected, the distribution of the overall volume of hydraulic liquid between the separations chambers 4000 simply results from the rotation of the rotor. When the weights of the separation bags 1000 are the same, the distribution of the hydraulic liquid is even. When they are not, the distribution of the hydraulic liquid is uneven, and the smaller the weight of a specific separation bag 1000, the larger the volume of the hydraulic fluid in the associated hydraulic chamber 510.

In the third stage, the blood within the separation bag 1000 is sedimented to a desired level.

At the onset of this stage, all pinch valve members 700, 710 are closed. The rotor is rotated at a second centrifugation speed (high sedimentation speed or "hard spin") for a predetermined period of time that is so selected that, whatever the hematocrit of the blood in the separation bag 1000, the blood sediments in each of the separation bag 1000 at the end of the selected period to a point where the hematocrit of the outer red blood cell layer is about 90 and the inner plasma layer does not substantially contain any more cells, the platelets and the white blood cells forming then an intermediary layer between the red blood cell layer and the plasma layer.

In the fourth stage a plasma component is transferred into the plasma component bag 200.

At the onset of this stage, the rotation speed is decreased to a third centrifugation speed, the four first pinch valve members 700 controlling access to the plasma component bag 200 are opened, and the pumping station 6000 is actuated so as to pump hydraulic liquid at a first constant flow rate into the hydraulic chambers 510 and consequently squeeze the separation bag 1000 and cause the transfer of plasma into the plasma component bags 200.

When blood cells are detected by the bag sensor 730 in the separation cell 4000 in which this detection occurs first, the pumping station 6000 is stopped and the corresponding first pinch valve member 700 is closed, either immediately of after a predetermined amount of time selected in view of the volume of plasma that it is desirable in the buffy coat component to be expressed in a next stage.

Following the closure of the first (first) pinch valve member 700 (i.e. the first pinch valve of the group of first pinch valve members 700) to close, the pumping station 6000 is actuated anew so as to pump hydraulic liquid at a second, lower, flow rate into the hydraulic chambers 510 and consequently squeeze the three separation bags 1000 whose outlet is not closed by the corresponding first pinch valve members 700.

When blood cells are detected by the bag sensor 730 in the separation cell 4000 in which this detection occurs second, the pumping station 6000 is stopped and the corresponding first pinch valve member 700 is closed (same timing as for the closing of the first (first) pinch valve member to close).

Following the closure of the second (first) pinch valve member 700 to close, the pumping station 6000 is actuated anew so as to pump hydraulic liquid at the second flow rate into the hydraulic chambers 510 and consequently squeeze the two separation bags 1000 whose outlet is not closed by the corresponding first pinch valve members 700.

When blood cells are detected by the bag sensor 730 in the separation cell 4000 in which this detection occurs third, the pumping station 6000 is stopped and the corresponding first pinch valve member 700 is closed (same timing as for the closing of the first (first) pinch valve member to close).

Following the closure of the third (first) pinch valve member 700 to close, the pumping station 600 is actuated anew so as to pump hydraulic liquid at the second flow rate into the hydraulic chambers 510 and consequently squeeze the separation bag 1000 whose outlet is not yet closed by the corresponding first pinch valve member 700.

When blood cells are detected by the bag sensor 730 in the separation cell 4000 in which this detection occurs last, the pumping station 6000 is stopped and the corresponding first pinch valve member 700 is closed (same timing as for the closing of the first pinch valve member to close).

In the plasma component transfer process described above, the transfer of the four plasma components starts at the same time, run in part simultaneously and stop independently of each other upon the occurrence of a specific event in each separation bag (detection of blood cells by the bag sensor).

The fourth stage ends when the four first pinch valve members 700 are closed.

In the fifth stage a buffy coat component is transferred into the buffy coat component bags 150.

The control unit 900 is programmed to start the fifth stage after the four first pinch valve members 700 are closed, upon receiving information from the last bag sensor 730 to detect blood cells.

At the onset of this stage, the rotation speed remains the same (third centrifugation speed), a first of the four second pinch valve members 710 controlling access to the buffy coat component bags 150 is opened, and the pumping station 6000 is actuated so as to pump hydraulic liquid at a third constant flow rate into the hydraulic chambers 510 and consequently squeeze the separation bag 1000 in the separation cell 4000 associated with the opened second pinch valve members 710 and cause the transfer of the buffy coat component into the buffy coat component bag 200 connected to this separation bag 1000.

After a predetermined period of time after blood cells are detected by the tube sensor 740 in the separation cell 4000 associated with the opened second pinch valve member 710, the pumping station 6000 is stopped and the second pinch valve member 710 is closed.

After the first (second) pinch valve member 710 has closed (i.e. the first pinch valve of the group of second pinch valve members 710), a second (second) pinch valve member 710 is opened, and a second buffy coat component is transferred into a buffy coat component bag 200, in the same way as above.

The same process is successively carried out to transfer the buffy coat component from the two remaining separation bags 1000 into the buffy coat component bag 200 connected thereto.

In the buffy coat component transfer process described above, the transfers of the four buffy coat components are successive, and the order of succession is predetermined. However, each of the second, third and four transfers starts following the occurrence of a specific event at the end of the previous transfer (detection of blood cells by the tube sensor 740 or closing of the second valve member 710).

The fifth stage ends when the four second pinch valve members 710 are closed.

In the sixth stage the centrifugation process is ended.

The control unit 900 is programmed to start the sixth stage after the four (second) pinch valve members 710 are closed, upon receiving information from the last tube sensor 740 to detect blood cells.

The rotation speed of the rotor is decreased until the rotor stops, the pumping station 6000 is actuated so as to pump the hydraulic liquid from the hydraulic chambers 510 at a high flow rate until the hydraulic chambers 510 are empty, and the first and second pinch valve members 700, 710 are actuated so as to seal and cut the tubes 170, 180. The red blood cells remain in the separation bag 1000.

When the fifth stage is completed, the four bag sets are removed from the separation apparatus and each bag set is separately handled manually.

The breakable stopper 100 blocking the communication between the separation bag 1000 and the tube 600 connected thereto is broken, as well as the breakable stopper 140 blocking the communication between the second satellite bag 300 and the tube 600. The storage solution contained in the second satellite bag 300 is allowed to flow by gravity through the leukoreduction filter 130 and into the separation bag 1000, where it is mixed with the red blood cells so as to lower the viscosity thereof. The content of the separation bag 1000 is then allowed to flow by gravity through the filter 130 and into the second satellite bag 300. The white blood cells are trapped by the filter 130, so that substantially only red blood cells are collected into the second satellite bag 300.

While using any whole blood processing devices like the ones described above, it has been observed that if whole blood is processed on the same day as it was collected, platelets clump or aggregate together and coat the blood separation bag. This leads to a significant reduction in platelet yield and decreased quality of the platelet component. A further observation is that platelet clumping/aggregation does not occur if whole blood is not processed the same day as collection, but is stored and processed the next day after being collected.

A further observation is that when separating blood into components using an automated whole blood processing device, leukoreduction procedures to remove white blood cells from red blood cells are more efficient in freshly collected blood rather than older blood.

From these observations, it appears that in procedures to separate blood components from whole blood using an automated whole blood processing device, optimal platelet collection and optimal red blood cell leukoreduction have different requirements.

The machines described above are used to separate previously collected whole blood into components. Previously collected whole blood could be separated into components either the same day as collection, or the next day after collection. How efficient separation of previously collected whole blood is however, depends upon several factors, such as the type of anticoagulant initially used during whole blood collection, and the starting pH of the whole blood to be separated. As discussed above, separation of platelets from whole blood on the same day the blood is collected is not as efficient as separation of platelets from blood which was collected the previous day. "Same day" blood is defined as blood which has been separated into components on the same day it was collected from a donor. "Next day" blood is defined as blood which has been separated into components on the day after collection.

In same day blood, platelets are more likely to aggregate and/or stick to the bag during the separation process as compared with next day blood. However, reduction of the amount of white blood cells in red blood cells via leukoreduction is more efficient in same day blood as compared to blood which has been previously collected, cooled and stored. Furthermore, many commercially available leukoreduction filters on the market are indicated for use at room temperature, which is the temperature of same day blood. Filters are more likely to plug during white blood cell filtration with next day cooled blood.

Same day blood has an average pH of between about 7.1 and 7.2. Next day blood has a pH of between about 6.8 to 6.9 at 37° C.

To address the seemingly antagonistic requirements for platelet collection and red blood cell leukoreduction, the pH of freshly collected whole blood may be modified to allow for immediate separation into the desired components, especially platelets. This could be done by changing the pH of the anticoagulant used in whole blood collection to make it more acidic. The term acidic pH means that the anticoagulant is buffered sufficiently such that the resultant mixture of whole blood and anticoagulant has a pH of around 6.8.

EXAMPLES

Having generally described the invention, the same will be more readily understood by reference to the following examples, which are provided by way of illustration and are not intended to be limiting.

Example 1

As discussed above, CPD is the anticoagulant currently used in whole blood collection. CPD has mean pH of around 7.0. The pH of CPD could be lowered to prevent platelets from clumping and sticking to the bag. An acid such as citric acid could be added to CPD to lower the resulting pH of the blood plus CPD to around 6.8. This would have the same effect as storing the blood overnight, which, as mentioned above, also lowers the pH of the blood. The effect would be immediate however, thereby allowing the freshly collected whole blood to be separated and the red blood cells to be leukoreduced efficiently on the same day as collection, while preventing platelets from clumping and/or sticking to the bag.

Whole blood and CPD was acidified by adding 60 g isotonic citric acid to 1000 mL of water. 4-5 g of this solution was added to 450 mL whole blood collected in 63 mL of CPD.

The acidifying solution could be added directly to whole blood and anticoagulant contained in bag 2 (see FIG. 1) or bag 1000 (see FIG. 4), or could be added to the whole blood and anticoagulant in the separation bag 5 (see FIG. 1). The acidifying solution could also be added to the anticoagulant before it is mixed with the collected whole blood.

In another embodiment, the pH of the anticoagulant could be lowered by adding $CO_2$ to the anticoagulant. The $CO_2$ could be added before the anticoagulant is added to the whole blood, or could be added after the whole blood is mixed with the anticoagulant. The $CO_2$ could be bubbled through the fluid using any commonly available means.

Example 2

Alternatively, an anticoagulant could be used which has a lower initial pH (is more acidic) then CPD. One such anticoagulant is ACDA, which has a mean pH of around 6.8. ACDA could be substituted for CPD.

Example 2 shows the platelet collection results obtained from units of whole blood separated on the same day as collection using either of the above described whole blood separation apparatuses. Whole blood units were collected in either ACDA or in CPD. Platelets were counted at 0 time after collection (T=0), 1 hour (T=1 hour) and 24 hours (T=24 hours) after collection. As can be seen from the table, units initially collected in ACDA produced a superior platelet yield (or cell count) and far less clumping (platelet recovery) then units initially collected in CPD.

|  | Platelet Count T = 0 hours | Platelet Recovery (%) T = 0 hours | Platelet Count T = 1 hour | Platelet Recovery (%) T = 1 hour | Platelet Count T = 24 hours | Platelet Recovery (%) T = 24 hours |
|---|---|---|---|---|---|---|
| Same day blood collected in ACDA | 8.9 × 10 | 77% | 9.4 × 10 | 81% | 9.9 × 10 | 88% |
| Same day blood collected in CPD | 3.4 × 10 | 37% | 5.9 × 10 | 64% | 6.2 × 10 | 67% |

As can be seen from Examples 1 and 2, by changing the pH of the anticoagulant used, the platelets will clump and/or stick to the bag much less than if anticoagulant having a higher pH is used. It can be extrapolated from this data that leukoreduction will be more efficient because the whole blood is separated into components on the same day it was collected. This principle is shown in Example 3 below.

Example 3

In Example 3, whole blood was collected in ACDA and separated the next day after overnight cold storage. Separated red blood cells were then leukoreduced (shown as POST-O/N storage in the table below). These results were compared to whole blood collected in ACDA and separated and leukoreduced the same day as collection (shown as PRE-O/N storage). As seen below, leukoreduction of next day blood collected in ACDA was not compromised. Data shown is the average of 6 samples.

|  | Platelet Count ($\times 10^3/\mu L$) | Platelet Count per Unit whole blood ($\times 10^{10}$) | WBC Count ($\times 10^3/\mu L$) | WBC Count per Unit whole blood ($\times 10^{10}$) |
|---|---|---|---|---|
| PRE-O/N storage WBC filtration | 60 | 1.38 | 3.23 | 0.74 |
| POST-O/N storage WBC filtration | 18.83 | 0.468 | 0.55 | 0.69 |

Example 4

If next day blood is to be separated and leukoreduced, in another embodiment, a buffering solution to increase the pH of the separated red blood cells may be added to the separated red blood cells before leukoreduction to enable more efficient filtration.

A solution which could increase the pH of red blood cells separated from next day blood could be added to separation bag 5 (see FIG. 1) or bag 1000 (see FIG. 4). Once the pH of the separated red blood cells reaches a pH of around 6.8, the red blood cells could then be leukoreduced. Examples of pH increasing solutions include buffers such as phosphate buffers which would raise the pH of the solution to between around 6.7 to 7.0.

In another embodiment, the pH of any solutions commonly used to store red blood cells could be increased to provide a more optimal pH for leukoreduction of red blood cells. A storage solution having an increased pH could have a pH of around 6.7 to 7.0. A storage solution having increased pH could be in bag 4 (see FIG. 1) or bag 300 (see FIG. 4).

It is understood for the purposes of this disclosure that various changes and modifications may be made to the invention that are will within the scope of the invention. Numerous other changes may be made which will readily suggest themselves to those skilled in the art and which are encompassed in the spirit of the methods disclosed herein.

The invention claimed is:

1. A method of collecting and separating whole blood into more than one component comprising the steps of:
   adding an anticoagulant having an acidic pH to a bag for collecting and/or separating whole blood before whole blood is collected in the bag; collecting whole blood in the bag;
   loading the bag containing anticoagulated whole blood on a rotor;
   spinning the bag on the rotor to separate the whole blood into more than one component; and
   expanding a hydraulic chamber on the rotor to squeeze the bag on the rotor to transfer the more than one component from the separation bag into a satellite bags;
   wherein the step of adding an anticoagulant further comprises adding CPD acidified with additional carbon dioxide.

2. The method of claim 1 wherein the step of adding an anticoagulant further comprises adding ACDA.

3. The method of claim 1 wherein the step of adding an anticoagulant further comprises adding CPD acidified with additional citric acid.

4. The method of claim 1 wherein the anticoagulated whole blood has a mean pH of between 6.7 and 7.0.

5. The method of claim 1 wherein the anticoagulated whole blood has a mean pH of around 6.8.

6. The method of claim 1 wherein the step of separating the whole blood into at least one component further comprises separating a red blood cell component.

7. The method of claim 6 wherein the separating step further comprises leukoreducing the separated red blood cell component.

8. The method of claim 1 wherein the separating step further comprises separating the whole blood on the same day the blood was collected.

9. A method of separating red blood cells from previously collected and stored whole blood comprising the steps of:
   collecting whole blood in CPD anticoagulant;
   storing the anticoagulated whole blood overnight;
   loading the anticoagulated whole blood on a rotor;
   spinning the rotor to separate the whole blood into at least a red blood cell component;
   expanding a hydraulic chamber on the rotor to squeeze the blood on the rotor to transfer at least the red blood cell component into a satellite bag; and
   increasing the pH of the separated red blood cell component in the satellite bag.

10. The method of claim 9 further comprising the step of leukoreducing the red blood cell component having increased pH.

11. The method of claim 9 wherein the step of increasing the pH of the separated red blood cell component further comprises adding a phosphate buffer.

12. The method of claim 9 wherein the step of increasing the pH of the separated red blood cell component further comprises adding a red blood cell storage solution that has an increased pH.

13. A method for separating whole blood into components comprising the steps of:
   collecting whole blood into a bag already containing an anticoagulant having an acidic pH;
   loading the bag containing the anticoagulant and whole blood onto a rotor;
   spinning the rotor to separate the whole blood into a plasma component, a platelet component and a red blood cell component;
   expanding a hydraulic chamber on the rotor to squeeze the bag on the rotor to transfer the plasma component into a second satellite bag;
   squeezing the bag on the rotor to transfer the platelet component into a first satellite bag; and
   squeezing the bag on the rotor to transfer the red blood cell component into a third satellite bag;
   further comprising a step of storing the collected whole blood and anticoagulant overnight before the separating step.

14. The method of claim 13 further including the step of increasing the pH of the red blood cell component.

15. The method of claim 14 wherein the step of increasing the pH of the red blood cell component further comprises adding a red blood cell storage solution which has an increased pH to increase the pH of the red blood cells.

16. The method of claim 13 further comprising a step of flowing the red blood cell component through a leukoreduction filter.

17. A method of collecting and separating whole blood into more than one component comprising the steps of:
   adding an anticoagulant having an acidic pH to a bag for collecting and/or separating whole blood before whole blood is collected in the bag;
   collecting whole blood in the bag;
   loading the bag containing anticoagulated whole blood on a rotor;
   spinning the bag on the rotor to separate the whole blood into more than one component; and
   expanding a hydraulic chamber on the rotor to squeeze the bag on the rotor to transfer the more than one component from the separation bag into a satellite bags;
   wherein the separating step further comprises separating the whole blood on the day after the blood was collected.

* * * * *